(12) United States Patent  (10) Patent No.: US 7,968,541 B2
Choi et al.  (45) Date of Patent: Jun. 28, 2011

(54) CRYSTALLINE FORM OF N-[[4-FLUORO-2-(5-METHYL-1H-1,2,4-TRIAZOL-1-YL)PHENYL]METHYL]-4,6,7,9-TETRAHYDRO-3-HYDROXY-9,9-DIMETHYL-4-OXO-PYRIMIDO[2,1-C][1,4]-OXAZINE-2-CARBOXAMIDE, SODIUM SALT MONOHYDRATE

(75) Inventors: Candice Y. Choi, Palisades Park, NJ (US); Alicia Tee Fuay Ng, East Haven, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 278 days.

(21) Appl. No.: 12/411,475

(22) Filed: Mar. 26, 2009

(65) Prior Publication Data

US 2009/0253692 A1 Oct. 8, 2009

Related U.S. Application Data

(60) Provisional application No. 61/039,989, filed on Mar. 27, 2008.

(51) Int. Cl.
*C07D 498/04* (2006.01)
*A61K 31/5383* (2006.01)
(52) U.S. Cl. ..................... 514/230.5; 544/105
(58) Field of Classification Search .................. 544/105; 514/230.5
See application file for complete search history.

(56) References Cited

U.S. PATENT DOCUMENTS

| 7,157,447 B2 | 1/2007 | Naidu et al. |
| 7,176,196 B2 | 2/2007 | Naidu et al. |
| 7,511,037 B2 | 3/2009 | Naidu et al. |

*Primary Examiner* — Kahsay T Habte
(74) *Attorney, Agent, or Firm* — James Epperson

(57) ABSTRACT

Disclosed is a crystalline form of N-[[4-fluoro-2-(5-methyl-1H-1,2,4-triazol-1-yl)phenyl]methyl]-4,6,7,9-tetrahydro-3-hydroxy-9,9-dimethyl-4-oxo-pyrimido[2,1-c][1,4]oxazine-2-carboxamide, sodium salt monohydrate. Also disclosed are at least one pharmaceutical composition comprising at least one crystalline form of N-[[4-fluoro-2-(5-methyl-1H-1,2,4-triazol-1-yl)phenyl]methyl]-4,6,7,9-tetrahydro-3-hydroxy-9,9-dimethyl-4-oxo-pyrimido[2,1-c][1,4]oxazine-2-carboxamide, sodium salt monohydrate, and at least one method of using at least one crystalline form of N-[[4-fluoro-2-(5-methyl-1H-1,2,4-triazol-1-yl)phenyl]methyl]-4,6,7,9-tetrahydro-3-hydroxy-9,9-dimethyl-4-oxo-pyrimido[2,1-c][1,4]oxazine-2-carboxamide, sodium salt monohydrate to treat AIDS or HIV infection.

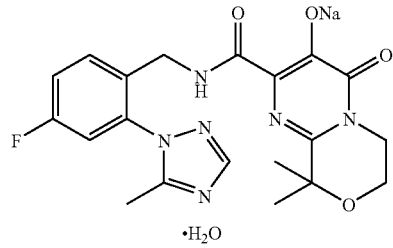

11 Claims, 3 Drawing Sheets

PXRD of sodium salt Form (mono-hydrate) of Compound I

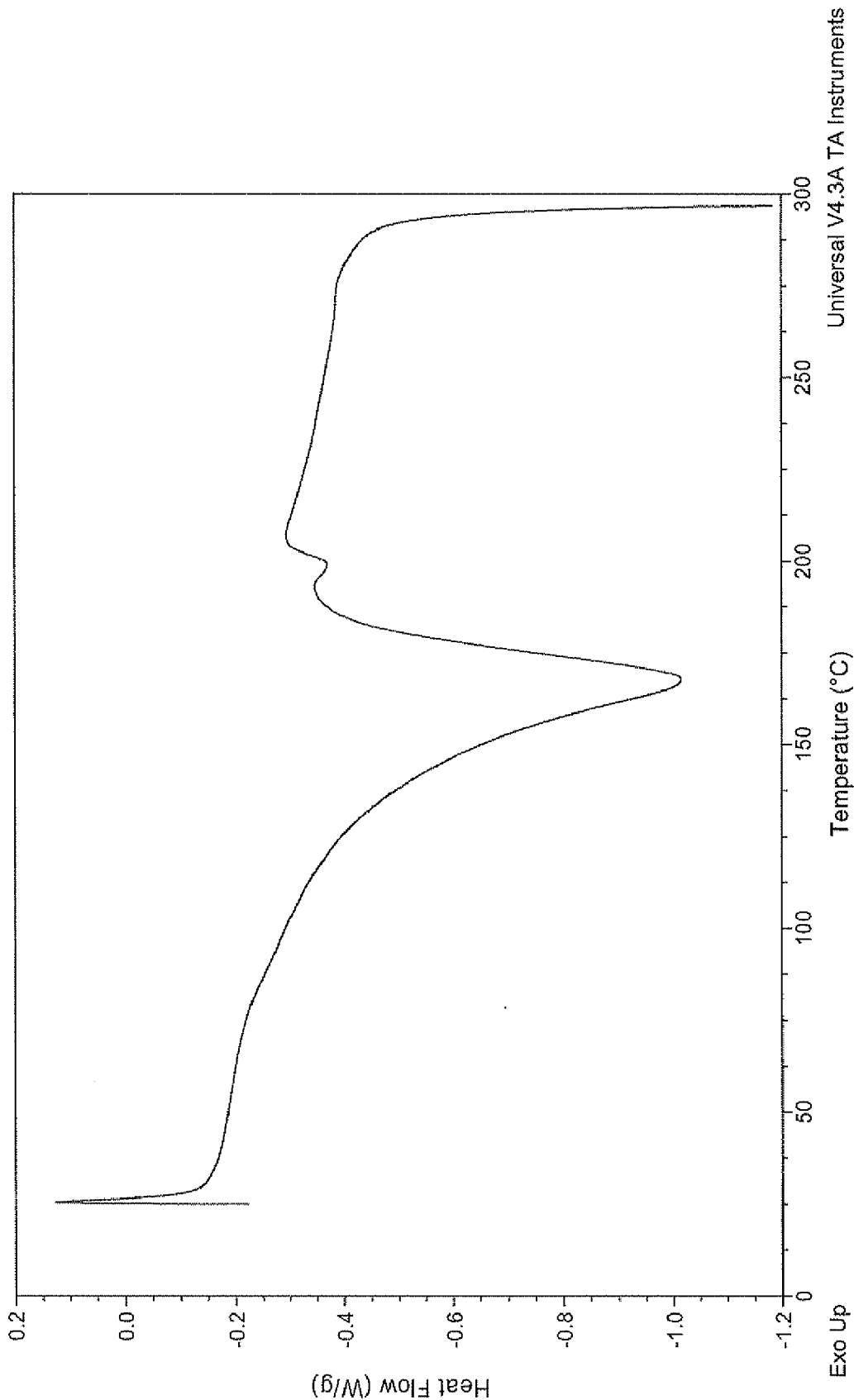

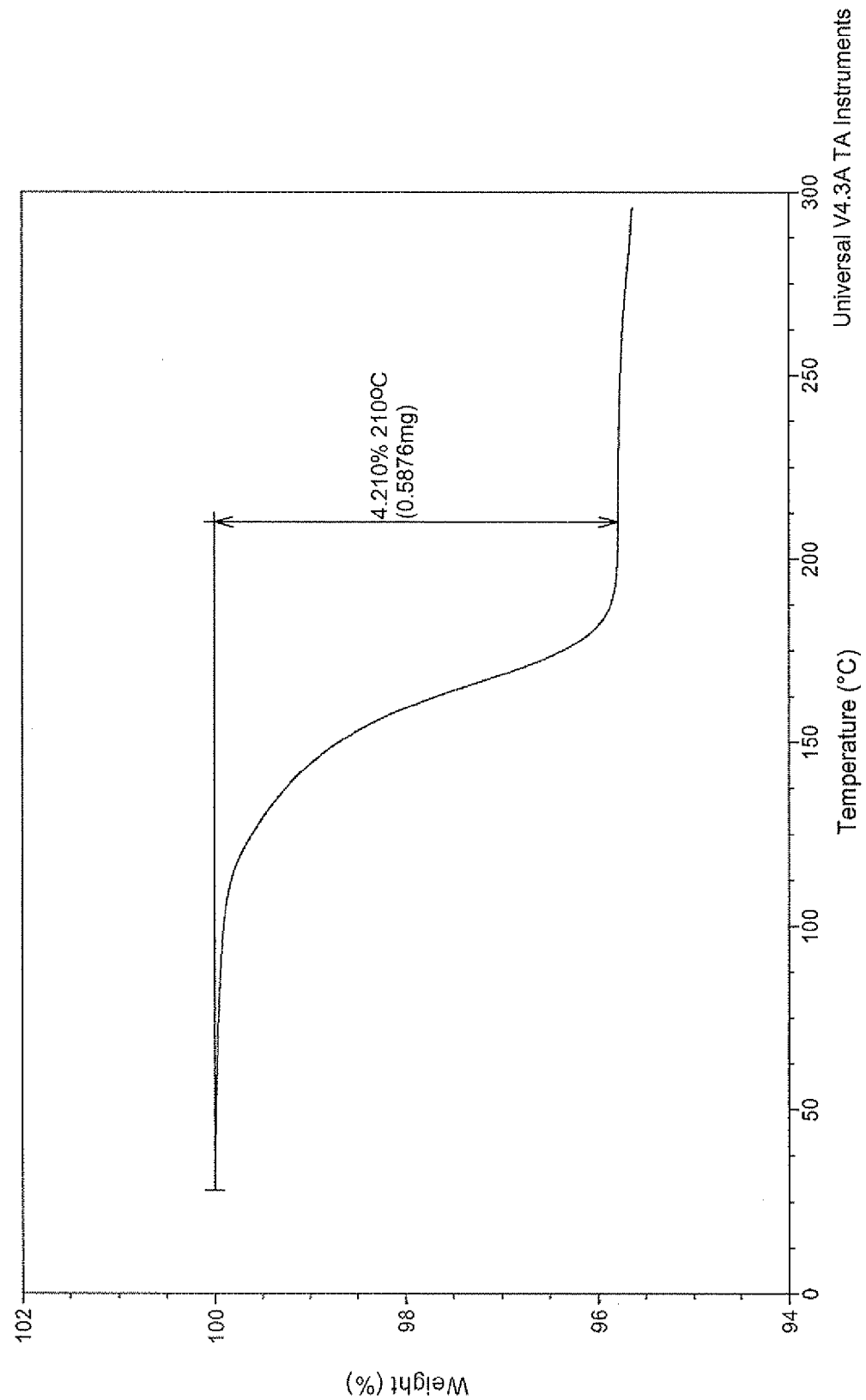

CRYSTALLINE FORM OF N-[[4-FLUORO-2-(5-METHYL-1H-1,2,4-TRIAZOL-1-YL)PHENYL]METHYL]-4,6,7,9-TETRAHYDRO-3-HYDROXY-9,9-DIMETHYL-4-OXO-PYRIMIDO[2,1-C][1,4]-OXAZINE-2-CARBOXAMIDE, SODIUM SALT MONOHYDRATE

CROSS-REFERENCE TO RELATED APPLICATIONS

This application claims the benefit of U.S. Provisional Application Ser. No. 61/039,989 filed Mar. 27, 2008.

BACKGROUND OF THE INVENTION

Disclosed is a crystalline form of N-[[4-fluoro-2-(5-methyl-1H-1,2,4-triazol-1-yl)phenyl]methyl]-4,6,7,9-tetrahydro-3-hydroxy-9,9-dimethyl-4-oxo-pyrimido[2,1-c][1,4]oxazine-2-carboxamide, sodium salt monohydrate. Also disclosed is at least one pharmaceutical composition comprising a crystalline form of N-[[4-fluoro-2-(5-methyl-1H-1,2,4-triazol-1-yl)phenyl]methyl]-4,6,7,9-tetrahydro-3-hydroxy-9,9-dimethyl-4-oxo-pyrimido[2,1-c][1,4]oxazine-2-carboxamide, sodium salt monohydrate, and at least one method of using a crystalline form of to treat AIDS or HIV infection.

[[4-fluoro-2-(5-methyl-1H-1,2,4-triazol-1-yl)phenyl]methyl]-4,6,7,9-tetrahydro-3-hydroxy-9,9-dimethyl-4-oxo-pyrimido[2,1-c][1,4]oxazine-2-carboxamide, sodium salt monohydrate, which has the structure of Formula (I):

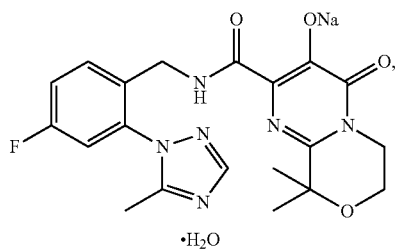

referred to herein as "Compound (I)", may be effective in treating AIDS or HIV infection. In at least one instance, Compound (I) was found to potently bind to and act as an antagonist to HIV integrase. Compound (I) is disclosed in U.S. Pat. No. 7,176,196, wherein said disclosure is hereby incorporated herein by reference.

Typically, in preparing a pharmaceutical composition, a form of the active ingredient is sought that has stability in handling. A difficulty regarding the free acid of Compound (I) is that it has a high susceptibility to ignition and risk for explosion. The present invention provides a form of Compound (I) that surprisingly affords a safer set of properties that can be useful in the manufacture of Compound (I).

SUMMARY OF THE INVENTION

Described herein is form of Compound (I):

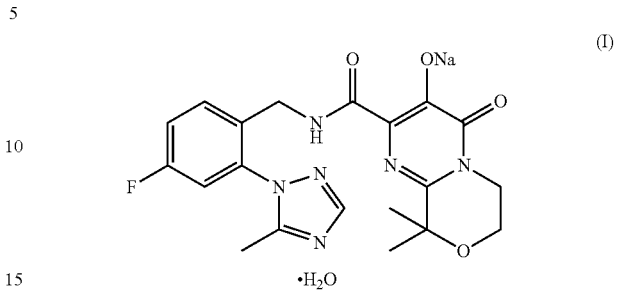

comprising Form H-1.

Further described herein is at least one pharmaceutical composition comprising a crystalline form of Compound (I), at least one pharmaceutically acceptable carrier and/or diluent; and optionally at least one other agent useful in treating AIDS or HIV infection.

Even further described herein is at least one method for treating AIDS or HIV infection, comprising administering to a patient in need thereof, a therapeutically effect amount of Compound (I), wherein Compound (I) is provided in a crystalline form comprising Form H-1; optionally administering either simultaneously or sequentially at least one other agent useful for treating AIDS or HIV infection.

BRIEF DESCRIPTION OF THE DRAWINGS

The invention is illustrated by reference to the accompanying drawings described below.

FIG. 2 shows a differential scanning calorimetry (DSC) thermogram of the H-1 Form of Compound (I).

FIG. 3 shows a thermogravimetric analysis (TGA) thermogram of the H-1 Form of Compound (I).

DETAILED DESCRIPTION OF THE INVENTION

Figure 1:
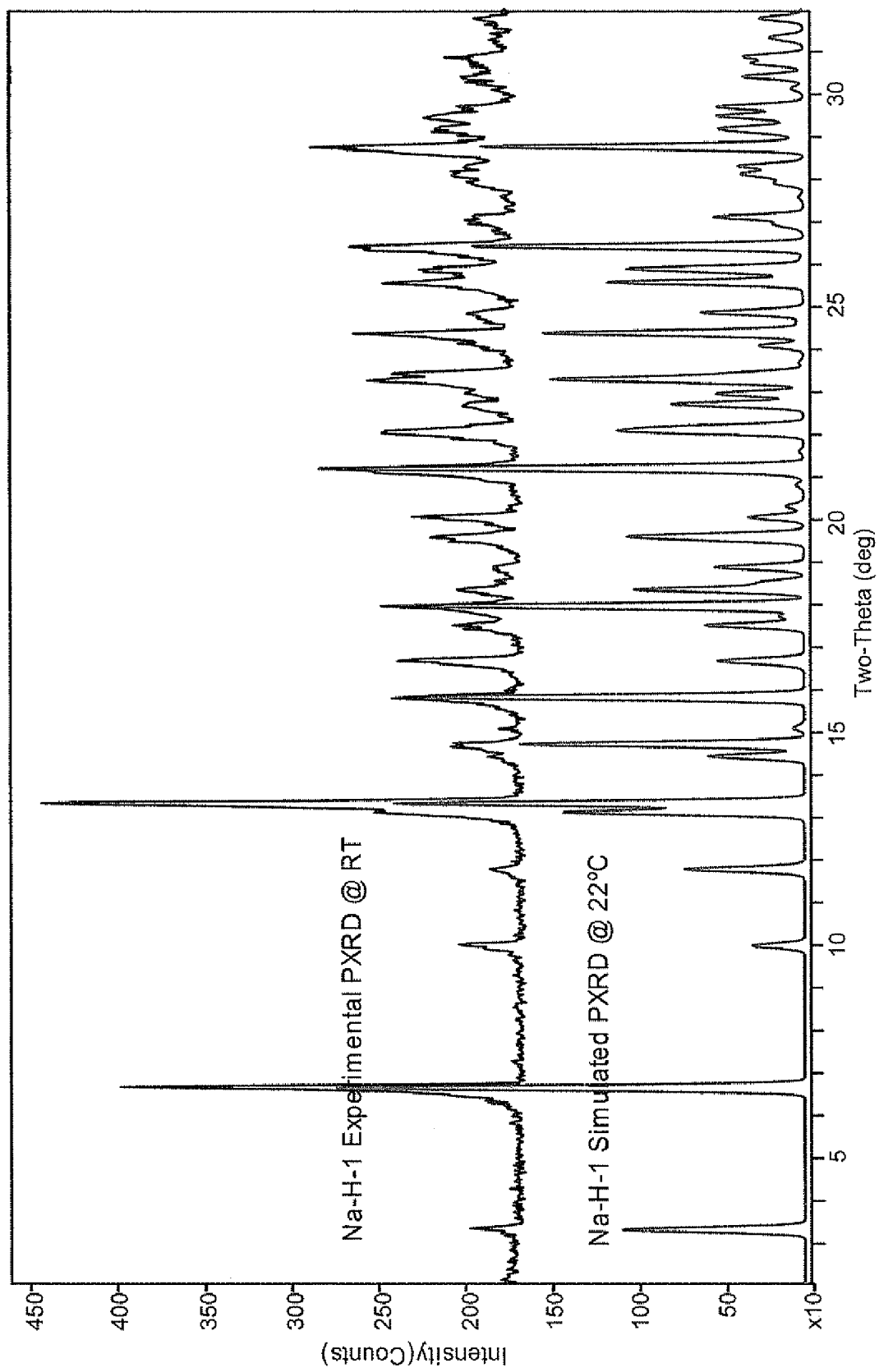
FIG. 1 shows observed (at room temperature (r.t.)) and simulated (at a Temperature (T) of about 22° C.) powder x-ray diffraction (PXRD) patterns (CuKα$\lambda$=1.5418 Å) of the H-1 Form of Compound (I).

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

The names used herein to characterize a specific form, e.g. "H-1" etc., are not to be limited so as to exclude any other substance possessing similar or identical physical and chemical characteristics, but rather such names are used as mere identifiers that are to be interpreted in accordance with the characterization information presented herein.

The definitions set forth herein take precedence over definitions set forth in any patent, patent application, and/or patent application publication incorporated herein by reference.

All numbers expressing quantities of ingredients, weight percentages, temperatures, and so forth that are preceded by the word "about" are to be understood as only approximations so that slight variations above and below the stated number may be used to achieve substantially the same results as the stated number. Accordingly, unless indicated to the contrary, numerical parameters preceded by the word "about" are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

All measurements are subject to experimental error and are within the spirit of the invention.

As used herein, "polymorphs" refer to crystalline forms having the same chemical structure but different spatial arrangements of the molecules and/or ions forming the crystals.

As used herein, "amorphous" refers to a solid form of a molecule and/or ions that is not crystalline. An amorphous solid does not display a definitive X-ray diffraction pattern with sharp maxima.

As used herein, the term "substantially pure" means the crystalline form of Compound (I) referred to contains at least about 90 wt. %, based on the weight of such crystalline form. The term "at least about 90 wt. %," while not intending to limit the applicability of the doctrine of equivalents to the scope of the claims, includes, but is not limited to, for example, about 90, 90, about 91, 91, about 92, 92, about 93, 93, about 94, 94, about 95, 95, about 96, 96, about 97, 97, about 98, 98, about 99, 99, and about 100 wt. %, based on the weight of the crystalline form referred to. The remainder of the crystalline form of Compound (I) may comprise other Form(s) of Compound (I) and/or reaction impurities and/or processing impurities that arise, for example, when the crystalline form is prepared.

For example, a crystalline form of Compound (I) may be deemed substantially pure if the crystalline form contains at least 90 wt. %, based on the weight of such crystalline form as measured by means that are at this time known and generally accepted in the art and less than about 10 wt. %, based on the weight of such crystalline form, of material comprising other Form(s) of Compound (I) and/or reaction impurities and/or processing impurities.

The presence of reaction impurities and/or processing impurities may be determined by analytical techniques known in the art, such as, for example, chromatography, nuclear magnetic resonance spectroscopy, mass spectrometry, and/or infrared spectroscopy.

As used herein, the parameter "molecules/asymmetric unit" refers to the number of molecules of Compound (I) in the asymmetric unit.

As used herein, the unit cell parameter "molecules/unit cell" refers to the number of molecules of Compound (I) in the unit cell.

When dissolved, the crystalline form of Compound (I) loses its crystalline structure, and is therefore referred to as a solution of Compound (I). At least one crystalline form of Compound (I) disclosed herein may be used to prepare at least one liquid formulation in which at least one crystalline form of Compound (I) is dissolved and/or suspended.

By "therapeutically effective amount" is meant an amount that when administered either alone, or in combination with an additional therapeutic agent is effective to prevent, suppress, and/or ameliorate a disease and/or condition and/or the progression of a disease and/or condition.

Disclosed herein is a crystalline form of Compound (I).

A crystalline form of Compound (I) comprises a sodium salt monohydrate crystalline form referred to herein as "Form H-1" or "H-1 Form".

In one embodiment, the H-1 Form is characterized by unit cell parameters approximately equal to the following:

| Cell dimensions: | a = 7.8283 (2 Å) |
| --- | --- |
| | b = 10.0489 (2 Å) |
| | c = 53.114 (Å) |
| | α = 90.0° |
| | β = 90.0° |
| | γ = 90.0° |

Space group: Pbca
Molecules of Compound (I)/asymmetric unit: 8
Volume = 4178.3 (2 Å$^3$)
Density (calculated) = 1.493 g/cm$^3$, wherein the unit cell parameters of Form H-1 are measured at a temperature of about 25° C.

In another embodiment, the H-1 Form is characterized by a simulated powder x-ray diffraction (PXRD) pattern substantially in accordance with the pattern shown in FIG. 1 and/or by an observed PXRD pattern substantially in accordance with the pattern shown in FIG. 1.

In yet another embodiment, the H-1 Form is characterized by a PXRD pattern (CuKαλ=1.5418 Å at a temperature of about 25° C.) comprising four or more, preferably five or more, 2θ values selected from: 3.3±0.2; 6.7±0.2; 10.0±0.2; 11.8±0.2; 13.3±0.2; 14.7±0.2; 15.8±0.2; 16.6±0.2; 21.2±0.2; and 22.1±0.2, wherein the PXRD pattern of Form H-1 is measured at a temperature of about 25° C.

In yet an even further embodiment, the H-1 Form is characterized by fractional atomic coordinates substantially as listed in Table 1.

TABLE 1

Atomic Coordinates (×10$^4$) and Equivalent Isotropic Displacement Parameters, Ueq (×10$^3$) for Form H-1.

| Atom | x | y | z | Ueq(Å$^2$) |
| --- | --- | --- | --- | --- |
| Na(1) | 2583(2) | 6288(1) | 1512(1) | 50(1) |
| N(2) | 4918(3) | 1965(2) | 616(1) | 40(1) |
| N(1) | 4207(3) | 1314(3) | 818(1) | 48(1) |
| N(3) | 5261(4) | −148(3) | 537(1) | 58(1) |
| C(1) | 4462(5) | 65(3) | 757(1) | 54(1) |
| C(2) | 5534(4) | 1064(3) | 451(1) | 48(1) |
| C(3) | 6391(5) | 1409(4) | 211(1) | 69(1) |
| C(4) | 4885(4) | 3389(3) | 604(1) | 38(1) |
| C(9) | 5602(4) | 4147(3) | 797(1) | 39(1) |
| C(10) | 6501(4) | 3498(3) | 1018(1) | 41(1) |
| C(5) | 4116(4) | 3976(3) | 397(1) | 47(1) |
| C(6) | 4085(5) | 5334(3) | 383(1) | 53(1) |
| C(8) | 5498(4) | 5524(3) | 772(1) | 48(1) |
| C(7) | 4759(5) | 6133(3) | 567(1) | 55(1) |
| F(1) | 3340(3) | 5920(2) | 178(1) | 77(1) |
| N(4) | 7077(3) | 4429(2) | 1208(1) | 41(1) |
| C(11) | 6009(4) | 4976(3) | 1375(1) | 35(1) |
| C(12) | 6806(3) | 5892(3) | 1561(1) | 31(1) |
| O(1) | 4443(2) | 4746(2) | 1370(1) | 43(1) |
| N(5) | 5691(3) | 6452(2) | 1734(1) | 31(1) |
| C(13) | 6276(3) | 7235(2) | 1908(1) | 28(1) |
| C(14) | 5033(3) | 7819(3) | 2100(1) | 32(1) |
| C(15) | 3910(4) | 6729(3) | 2211(1) | 41(1) |
| C(16) | 3949(4) | 8905(3) | 1980(1) | 44(1) |
| O(2) | 5937(2) | 8334(2) | 2316(1) | 40(1) |
| C(17) | 7297(4) | 9200(3) | 2248(1) | 44(1) |
| C(18) | 8699(4) | 8428(3) | 2122(1) | 38(1) |

TABLE 1-continued

Atomic Coordinates (×10$^4$) and Equivalent Isotropic
Displacement Parameters, Ueq (×10$^3$) for Form H-1.

| Atom | x | y | z | Ueq(Å$^2$) |
|---|---|---|---|---|
| N(6) | 7990(3) | 7558(2) | 1924(1) | 29(1) |
| C(19) | 9182(3) | 7015(2) | 1764(1) | 31(1) |
| C(20) | 8561(3) | 6126(3) | 1564(1) | 31(1) |
| O(3) | 9700(2) | 5638(2) | 1417(1) | 42(1) |
| O(4) | 10717(2) | 7256(2) | 1795(1) | 42(1) |
| O(5) | 2873(4) | 7804(3) | 1187(1) | 77(1) |
| H(1) | 4112 | −631 | 861 | 65 |
| H(3A) | 7100 | 681 | 158 | 103 |
| H(3B) | 7082 | 2188 | 234 | 103 |
| H(3C) | 5544 | 1581 | 84 | 103 |
| H(10A) | 5727 | 2865 | 1096 | 49 |
| H(10B) | 7479 | 3005 | 956 | 49 |
| H(5) | 3632 | 3458 | 271 | 57 |
| H(8) | 5947 | 6055 | 899 | 57 |
| H(7) | 4719 | 7055 | 553 | 66 |
| H(4) | 8142 | 4637 | 1214 | 50 |
| H(15A) | 4612 | 6093 | 2297 | 61 |
| H(15B) | 3300 | 6291 | 2077 | 61 |
| H(15C) | 3111 | 7114 | 2327 | 61 |
| H(16A) | 3215 | 9292 | 2105 | 66 |
| H(16B) | 3268 | 8527 | 1848 | 66 |
| H(16C) | 4681 | 9580 | 1911 | 66 |
| H(17A) | 7740 | 9634 | 2397 | 52 |
| H(17B) | 6877 | 9883 | 2135 | 52 |
| H(18A) | 9515 | 9040 | 2048 | 45 |
| H(18B) | 9294 | 7892 | 2246 | 45 |

In a still further embodiment, H-1 Form is characterized by a differential scanning calorimetry (DSC) thermogram substantially in accordance with that shown in FIG. 2.

In still yet a farther embodiment, the H-1 Form is characterized by a thermogravimetric analysis (TGA) thermogram having weight loss in the range of from about weight loss of ca. 3.9-4.4 wt. %, based on the weight of the sample of Form H-1, upon being heated to a temperature of about 210° C.

In still another embodiment, the H-1 Form exhibits a TGA thermogram substantially the same as shown in FIG. 3.

In still yet an even further embodiment, the form H-1 of Compound (I) is substantially pure.

In still yet another embodiment, the form H-1 of Compound (I) contains at least about 90 wt. %, preferably at least about 95 wt. %, and more preferably at least about 99 wt. %, based on weight of the first crystalline form, Form H-1.

In yet another embodiment, a substantially pure form of H-1 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, a substantially pure form of H-1 has substantially pure phase homogeneity with less than about 1% of the total peak area of the experimentally measured PXRD pattern arising from peaks that are absent from the simulated PXRD pattern.

In another embodiment, the form H-1 of Compound (I) consists essentially of Form H-1. The form of this embodiment may comprise at least about 90 wt. %, preferably at least about 95 wt. %, and more preferably at least about 99 wt. %, based on the weight of Form H-1.

In yet another embodiment, a pharmaceutical composition comprises Form H-1; and at least one pharmaceutically-acceptable carrier and/or diluent.

In still another embodiment, a pharmaceutical composition comprises a substantially pure form of H-1; and at least one pharmaceutically-acceptable carrier and/or diluent.

In still an even further embodiment, a therapeutically effective amount of Form H-1 is combined with at least one pharmaceutically acceptable carrier and/or diluent to provide at least one pharmaceutical composition.

Still yet a further embodiment provides a method for treating AIDS or HIV infection comprising administering Compound (I) to a patient in need thereof, wherein Compound (I) is provided in a form comprising Form H-1. A therapeutically effective amount of Compound (I) can be administered in the method of this embodiment. In one embodiment, the patient is a human.

One embodiment provides the use of Compound (I) in the manufacture of a medicament for treatment of a proliferative disease, wherein Compound (I) is provided in a crystalline form comprising Form H-1. The medicament can comprise a therapeutically effective amount of Compound (I), wherein Compound (I) is provided in a crystalline form comprising Form H-1.

One embodiment provides Compound (I), for use in therapy in treating AIDS or HIV infection, wherein Compound (I) is provided in a crystalline form comprising Form H-1.

Pharmaceutical Composition and Methods of Use

In 2007, Reltagravir, an HIV integrase inhibitor, was approved by the US FDA for treating AIDS and HIV infection. Compound I has demonstrated inhibition of HIV integrase, See U.S. Pat. No. 7,176,196.

Accordingly, another aspect of the invention is a method for treating AIDS or HIV infection in a human patient comprising administering a therapeutically effective amount of Form H-1 of Compound (I) with a pharmaceutically acceptable carrier.

Another aspect of the invention is a method for treating AIDS or HIV infection in a human patient comprising the administration of a therapeutically effective amount of Form H-1 of Compound (I) with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt or solvate thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable salt or solvate thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt or solvate thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt or solvate thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt or solvate thereof.

Another aspect of the invention is a method wherein the agent is a CXCR4 inhibitor.

Another aspect of the invention is a method wherein the CXCR4 inhibitor is AMD-3100, or a pharmaceutically acceptable salt or solvate thereof.

Another aspect of the invention is a method wherein the agent is an HIV budding or maturation inhibitor.

Another aspect of the invention is a method wherein the budding or maturation inhibitor is PA-457, or a pharmaceutically acceptable salt, or solvate thereof.

Another aspect of the invention is a method wherein the agent is an HIV integrase inhibitor.

Another aspect of the invention is a method wherein the integrase inhibitor is raltegravir.

Another aspect of the invention is a pharmaceutical composition comprising a therapeutically effective amount of Form H-1 of Compound (I) and at least one pharmaceutically acceptable carrier and/or diluent.

Another aspect of the invention is a pharmaceutical composition comprising a therapeutically effective amount of Form H-1 of Compound (I) with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt or solvate thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt or solvate thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt or solvate thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt or solvate thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt or solvate thereof.

Another aspect of the invention is a method wherein the agent is a CXCR4 inhibitor.

Another aspect of the invention is a method wherein the CXCR4 inhibitor is AMD-3100 or a pharmaceutically acceptable salt or solvate thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt or solvate thereof.

Another aspect of the invention is the composition wherein the agent is an HIV integrase inhibitor.

Another aspect of the invention is the composition wherein the HIV integrase inhibitor is raltegravir.

"Combination," "coadministration," "concurrent," and similar terms referring to the administration of a form of Compound I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

Compound (I) is generally given as a pharmaceutical composition comprised of a therapeutically effective amount of Compound I and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/ml, 10 mg/mL, 25 mg/mL, 50 mg/mL, and 100 mg/mL.

Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where Compound I is given in combination therapy. That is, of a form of Compound I can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, Compound I will generally be given in a daily dose of 1-100 mg/kg body weight daily in conjunction with other agents. The other agents generally will be given in the amounts used therapeutically. The specific dosing regime, however, will be determined by a physician using sound medical judgement.

Experimental Methods

Crystalline forms may be prepared by a variety of methods, including, but not limited to, for example, crystallization or recrystallization from a suitable solvent mixture; sublimation; growth from a melt; solid state transformation from another phase; crystallization from a supercritical fluid; and jet spraying. Techniques for crystallization or recrystallization of crystalline forms from a solvent mixture include, but are not limited to, for example, evaporation of the solvent; decreasing the temperature of the solvent mixture; crystal seeding a supersaturated solvent mixture of the compound and/or a salt from thereof; freeze drying the solvent mixture; and adding antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Ind. (1999).

In a crystallization technique in which solvent is employed, the solvent(s) are typically chosen based on one or more factors including, but not limited to, for example, solubility of the compound; crystallization technique utilized; and vapor pressure of the solvent. Combinations of solvents may be employed. For example, the compound may be solibilized in a first solvent to afford a solution to which antisolvent is then added to decrease the solubility of the compound in the solution and precipitate the formation of crystals. An antisolvent is a solvent in which a compound has low solubility.

In one method that can be used in preparing crystals, a compound is suspended and/or stirred in a suitable solvent to afford a slurry, which may be heated to promote dissolution. The term "slurry", as used herein, means a saturated solution of the compound, wherein such solution may contain an additional amount of compound to afford a heterogeneous mixture of compound and solvent at a given temperature.

Seed crystals may be added to any crystallization mixture to promote crystallization. Seeding may be employed to control growth of a particular polymorph and/or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science*, 1971, 26, 369-377. In general, seeds of small size are needed to effectively control the growth of crystals in the batch, Seeds of small size may be generated by sieving, milling, or micronizing large crystals, or by micro-crystallizing a solution. In the milling or micronizing of crystals, care should be taken to avoid changing crystallinity from the desired crystalline form (i.e., changing to an amorphous or other polymorphic form).

A cooled crystallization mixture may be filtered under vacuum and the isolated solid product washed with a suitable solvent, such as, for example, cold recrystallization solvent. After being washed, the product may be dried under a nitrogen purge to afford the desired crystalline form. The product may be analyzed by a suitable spectroscopic or analytical technique including, but not limited to, for example, solid state nuclear magnetic resonance; differential scanning calorimetry (DSC); and powder x-ray diffraction (PXRD) to assure the preferred crystalline form of the compound has been formed. The resulting crystalline form may be produced in an amount greater than about 70 wt. % isolated yield, based on the weight of the compound originally employed in the crystallization procedure, and preferably greater than about 90 wt. % isolated yield. Optionally, the product may be delumped by being comilled or passed through a mesh screen.

Crystalline forms of Compound (I) including, but not limited to, for example, the Form described herein, may be prepared directly from the reaction medium produced via the final process step employed in preparing Compound (I). For example, crystalline form(s) of Compound (I) could be produced by employing a solvent or a mixture of solvents in the final process step employed in preparing Compound (I). Alternatively, crystalline forms of Compound (I) may be obtained by distillation or solvent addition techniques. Suitable solvents for this purpose include, but are not limited to, for example, the aforementioned nonpolar and polar solvents, wherein polar solvents include, but are not limited to, for example, protic polar solvents, such as, for example, alcohols and aprotic polar solvents, such as, for example, ketones.

The presence of more than one crystalline form and/or polymorph in a sample may be determined by techniques, including, but not limited to, for example, PXRD and solid state nuclear magnetic resonance spectroscopy. For example, the presence of extra peaks when an experimentally measured PXRD pattern is compared to a simulated PXRD pattern may indicate more than one crystalline form and/or polymorph in the sample. The simulated PXRD may be calculated from single crystal x-ray data. See, for example, Smith, D. K., "*A FORTRAN Program for Calculating X-Ray Powder Diffraction Patterns*," Lawrence Radiation Laboratory, Livermore, Calif., UCRL-7196 (April 1963).

Crystalline forms of Compound (I), including, but not limited to, those described herein according to the invention may be characterized using a variety of techniques well known to person(s) of ordinary skill in the art. For example, the single x-ray diffraction technique may, under standardized operating conditions and temperatures, be used to characterize and distinguish crystalline form(s) of Compound (I). Such characterization may, for example, be based on unit cell measurements of a single crystal of the desired form at a fixed analytical temperature. The approximate unit cell dimensions in Angstroms (Å), as well as the crystalline cell volume, space group, molecules per cell, and crystal density may be measured, for example, at a sample temperature of 25° C. A detailed description of unit cells is provided in Stout & Jensen, *X-Ray Structure Determination: A Practical Guide*, Macmillan Co., N.Y. (1968), Chapter 3, which is hereby incorporated herein by reference.

Additionally, the unique spatial arrangement of atoms in a crystalline lattice may be characterized according to the observed fractional atomic coordinates of such atoms.

Another means of characterizing the crystalline structure of the subject form is by PXRD analysis, the actual diffraction profile of such form is compared to a simulated profile representing pure powder material. Preferably, the actual and simulated profiles are both run at the same analytical temperature, and the subsequent measurements characterized as a series of 2θ values (usually four or more).

Other means of characterizing a crystalline form that may be used include, but are not limited to, for example, solid state nuclear magnetic resonance (NMR); DSC; thermography; gross examination of the crystalline or amorphous morphology; and combinations thereof.

At least one crystalline form of Compound (I) described herein was analyzed using at least one of the testing methods described hereinbelow.

Single Crystal X-Ray Measurements

Data was collected with a Bruker-Nonius CAD4 serial diffractometer (Bruker AXS, Inc., Madison, Wis.). Unit cell parameters were obtained through least-squares analysis of the experimental diffractometer settings of 25 high-angle reflections. Intensities were measured using Cu Kα radiation (λ=1.5418 Å) at a constant temperature with the θ-2θ variable scan technique and were corrected only for Lorentz-polarization factors. Background counts were collected at the extremes of the scan for half of the time of the scan. Alternately, single crystal data was collected with a Bruker-Nonius Kappa CCD 2000 system using Cu Kα radiation (λ=1.5418 Å). Indexing and processing of the measured intensity data were carried out with the HKL2000 software package (Otwinowski, Z. and Minor, W., in *Macromolecular Crystallography*, eds. Carter, W. C. Jr. and Sweet, R. M., Academic Press, NY, 1997) in the Collect program suite (Collect: Data collection software, R. Hooft, Nonius B.V., 1998). When indicated, crystals were cooled in the cold stream of an Oxford Cryosystems Cryostream Cooler (Oxford Cryosystems, Inc., Devens, Mass.) during data collection.

The structures were solved by direct methods and refined on the basis of observed reflections using either the SDP software package (SDP Structure Determination Package, Enraf-Nonius, Bohemia, N.Y.) with minor local modifications or the crystallographic package maXus (maXus Solution and Refinement Software Suite: S. Mackay, C. J. Gilmore, C. Edwards, M. Tremayne, N. Stewart, and K. Shankland).

The derived atomic parameters (coordinates and temperature factors) were refined through full matrix least-squares. The function minimized in the refinements was $\Sigma_w(|F_O|-|F_C|)^2$. R is defined as $\Sigma \; ||F_O|-|F_C||/\Sigma|F_O|$ while $R_w=[\Sigma_w (|F_O|-|F_C|)^2/\Sigma_w|F_O|^2]^{1/2}$ where w is an appropriate weighting function based on errors in the observed intensities. Difference maps were examined at all stages of refinement. Hydrogen atoms were introduced in idealized positions with isotropic temperature factors, but no hydrogen parameters were varied.

Simulated PXRD patterns were generated from the single crystal atomic parameters at the data collection temperature, unless noted otherwise. (Yin. S.; Scaringe, R. P.; DiMarco, J.; Galella, M. and Gougoutas, J. Z., *American Pharmaceutical Review*, 2003, 6, 2, 80).

Powder X-Ray Diffraction (PXRD) Measurements—Method A

About 200 mg of the sample was packed by the backloading method into a Philips PXRD-sample holder. The sample holder was transferred to a Philips MPD unit (45 KV, 40 mA, Cu Kα), and the data was subsequently collected at room temperature in the 2 to 32 2-theta range (continuous scanning mode, scanning rate 0.03 degrees/sec., auto divergence and anti scatter slits, receiving slit: 0.2 mm, sample spinner: ON).

Powder X-Ray Diffraction Measurements—Method B

PXRD data was obtained using a Bruker C2 GADDS. The radiation was Cu Kα (40 KV, 50 mA). The sample-detector distance was 15 cm. Powder samples were placed in sealed glass capillaries of 1 mm or less in diameter, and the capillary was rotated during data collection. Data were collected for $3 \leq 2\theta \leq 35°$ with a sample exposure time of at least about 2000 seconds, The resulting two-dimensional diffraction arcs were integrated to create a traditional 1-dimensional PXRD pattern with a step size of 0.02 degrees 2θ in the range of 3 to 35 degrees 2θ.

Differential Scanning Calorimetry (DSC) (Sealed Pan)

DSC experiments were performed in a TA Instruments™ model Q1000 or 2920. The sample (about 2-6 mg) was weighed in a pinpricked hermetically sealed aluminum pan and, after being accurately recorded to a hundredth of a milligram, was transferred to the DSC. The instrument was purged with nitrogen gas at 50 mL/min. Data were collected between room temperature and about 350° C. at a heating rate of about 10° C./min. The plot was made with the endothermic peaks pointing down.

Thermal Gravimetric Analysis (TGA) (Sealed Pan)

TGA experiments were performed in a TA Instruments™ model Q500 or 2950. The sample (about 10-30 mg) was placed in a pinpricked hermetically sealed aluminum pan on a platinum pan, both previously tared. The weight of the sample was measured accurately and recorded to a thousand of a milligram by the instrument. The furnace was purged with nitrogen gas at 100 mL/min. Data was collected between room temperature and about 350° C. at a heating rate of about 10° C./min.

Example 1

Preparation of Compound I. The Synthesis of the Free Acid is Illustrated in Scheme 1 and described in U.S. Pat. No. 7,176,196.

Scheme 1.

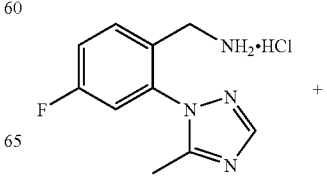

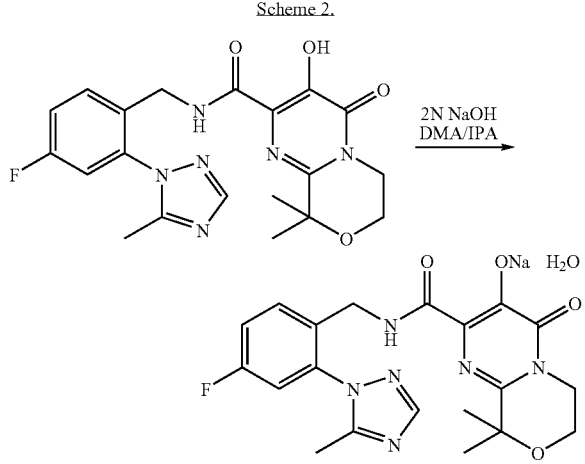

The synthesis of the sodium salt monohydrate is illustrated in Scheme 2.

The free acid (34 g; 1.00 equiv; 79.36 mmoles) was added to the flask. Dimethylacetamide (340 mL) was added and stirring started. The mixture was heated to 60° C. with stirring when a solution was formed. The solution was stirred for 30 min at 60° C. To the solution, 2N Sodium Hydroxide (44.00 mL; 45.75 g; 87.99 mmoles; 1.10 eq.) was added at 60° C. The mixture was stirred for 30 min at 60° C. The mixture was seeded with 1% seed load of the sodium salt monohydrate (0.34 g, 0.79 mmol) and stirred for 1 hr at 60° C. Isopropyl Alcohol (374 mL) was added at 60° C. to the mixture over 2 hrs. The mixture was stirred for 30 min at 60° C., and then cooled to 20° C. over 2 hrs. via a cooling ramp. The mixture was stirred at least 3 hrs. at 20° C. prior to filtration. The mixture was filtered. The solid was washed four times with a 90:10 isopropyl alcohol-water mixture (150 mL each wash). The solid product was dried in a vacuum oven at ≦60° C. overnight. The product (33.72 g; 0.91 equiv; 71.99 mmoles; 90.71% yield) was obtained as a white solid. HPLC purity was >99.6 AP. Anal calcd for $C_{20}H_{22}FN_6NaO_5$: C, 51.28, H, 4.73, N, 17.94. Found: C, 51.38, H, 4.48, N, 17.91; mp: 298° C.

Dust Hazard Data

"μm" means micrometer. "gm" means gram. "cc" means cubic centimeter. "gm/cc" means gram per cubic centimeter. "Kst" is the deflagration index of a dust expressed in bar-meter per second. "bar-m/s" means bar meter per sec. "bar/s" means bar per second. "mJ" means millijoules. "St" is the general classification designation for explosible dusts: "St-2" is classified as a strong explosion designation and has Kst>200 bar-m/sec; "St-1" is not classified as a strong explosion and has Kst<200 bar-m/sec.

Particle analysis. The free acid was tested for particle size using an Aerosizer instrument (TSI Inc., Amhest, Mass.) and was found to contain 95%<32.9 μm, with a mean value of 16.3 μm. The bulk and true densities were found to be 0.34 gm/cc and 1.40 g/cc respectively. The sample was checked for moisture content by placing 5 gm in a vacuum oven at 60° C. for six hours and checking weight loss. The free acid lost 0.22% of its initial weight.

The sodium salt monohydrate was tested for particle size using an Aerosizer instrument and was found to contain 95%<33.6 μm, with a mean value of 14.8 μm. The bulk and true densities were found to be 0.42 gm/cc and 1.53 gm/cc, respectively. The sample was checked for moisture content by placing 5 gm in a vacuum oven at 60° C. for six hours and checking weight loss. The salt monohydrate lost 0.18% of its initial weight.

Dust Hazard Analysis.

The dust hazard analysis results for both forms are summarized in the Table 2.

TABLE 2

| Dust Explosion Risk | Free acid | Sodium salt |
| --- | --- | --- |
| Minimum Ignition Energy | >3, <10 mJ | >500 mJ |
| Minimum Ignition Temperature | >540° C., <560° C. | >600° C. |
| Explosion Severity (Max rate) | 878 bar/s | 154 bar/s |
| Explosion Severity (Max Pressure) | 8.2 bar | 1.5 bar |
| Kst value | 238 bar · m/s | na |
| Charge Decay Time Estimation | 5.5 hours | 33 minutes |
| St Classification | St-2 | St-1 |

The free acid was extremely susceptible to igniting as a dust cloud under certain conditions due to low minimum ignition energy. Twenty liter sphere testing (see Proust, C.; Accorsi, A.; Dupont, L. *Journal of Loss prevention in the Process Industries*, vol. 20, 2007.) places the sample in the St-2 (strong explosion) class with a Kst value of 238 bar-m/s.

The sodium salt had low susceptibility to ignition as a dust cloud. Therefore, twenty liter sphere testing was not required. The data indicated that the salt exhibits weak to moderate explosion characteristics and the St designation is assumed to be St-1.

What is claimed is:
1. A crystalline form of Compound (I):

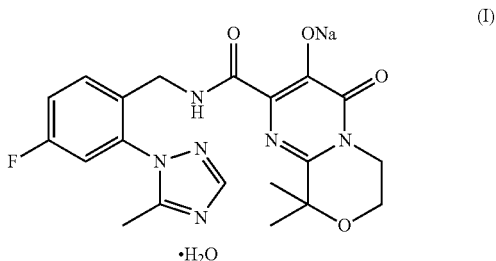

comprising Form H-1, wherein said Form H-1 is characterized by:

a) a powder x-ray diffraction pattern comprising five or more 2θ values (CuKαλ=1.5418 Å) selected from: 3.3±0.2; 6.7±0.2; 10.0±0.2; 11.8±0.2; 13.3±0.2; 14.7±0.2; 15.8±0.2; 16.6±0.2; 21.2±0.2; and 22.1±0.2, wherein the powder x-ray diffraction pattern of said crystalline form is measured at a temperature of about 25° C.;

b) unit cell parameters substantially equal to the following:

| Cell dimensions: | a = 7.8283 (2 Å) |
|---|---|
| | b = 10.0489 (2 Å) |
| | c = 53.114 (Å) |
| | α = 90.0° |
| | β = 90.0° |
| | γ = 90.0° |

Space group: Pbca
Molecules of Compound (I)/asymmetric unit: 8
Volume = 4178.3 (2 Å$^3$)
Density (calculated) = 1.493 g/cm$^3$, wherein the unit cell parameters of said crystalline form are measured at a temperature of about 25° C.;

c) a melting point in the range of about 298° C.; and/or d) a thermogravimetric analysis thermogram having weight loss in the range of from about 3.9 to about 4.4 weight % upon heating to a temperature of about 210° C.

2. A crystalline form of Compound (I):

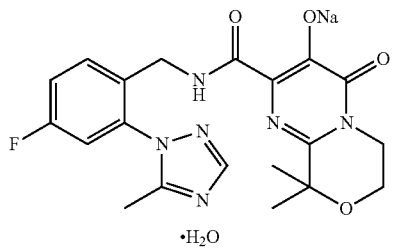

(I)

·H$_2$O comprising Form H-1, wherein said Form is characterized by a simulated powder x-ray diffraction pattern substantially as shown in FIG. 1; and/or an observed powder x-ray diffraction pattern substantially as shown in FIG. 1.

3. The crystalline form according to claim 1 or 2, consisting essentially of said Form H-1.

4. The crystalline form according to claim 1 or 2, wherein said crystalline form is substantially pure.

5. The crystalline form according to claim 1 or 2, wherein at least about 90 wt. % of said crystalline form is comprised of Form H-1.

6. A pharmaceutical composition comprising crystalline form H-1 of Compound (I):

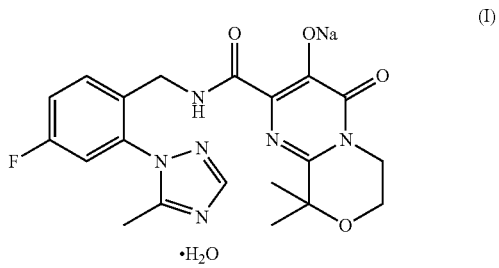

(I)

·H$_2$O and at least one pharmaceutically acceptable carrier and/or diluent.

7. The pharmaceutical composition according to claim 6, wherein said crystalline form is in a substantially pure form.

8. The composition of claim 6 further comprising a therapeutically effective amount at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

9. A method for treating HIV infection in a patient comprising administering a therapeutically effective amount of crystalline form H-1 of Compound (I):

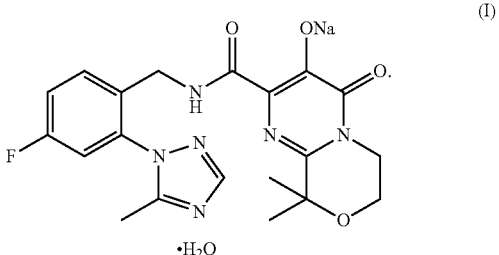

(I)

·H$_2$O

10. The method of claim 9, wherein the crystalline form is in a substantially pure form.

11. The method of claim 9 further comprising administering a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *

UNITED STATES PATENT AND TRADEMARK OFFICE
CERTIFICATE OF CORRECTION

PATENT NO. : 7,968,541 B2
APPLICATION NO. : 12/411475
DATED : June 28, 2011
INVENTOR(S) : Candice Y. Choi et al.

It is certified that error appears in the above-identified patent and that said Letters Patent is hereby corrected as shown below:

In the Specification:

Column 4, line 13, change "c = 53.114 (Å)" to -- c = 53.114 (1Å) --.

Column 4, line 18, change "Molecules of Compound (I)/asymmetric unit: 8" to -- Molecules of Compound (I)/unit cell: 8 --.

In the Claims:

Claim 1:

Column 15, line 13, change "c = 53.114 (Å)" to -- c = 53.114 (1Å) --.

Column 15, line 18, change "Molecules of Compound (I)/asymmetric unit: 8" to -- Molecules of Compound (I)/unit cell: 8 --.

Signed and Sealed this
Twentieth Day of December, 2011

David J. Kappos
*Director of the United States Patent and Trademark Office*